United States Patent
Hanai et al.

(10) Patent No.: US 8,691,158 B2
(45) Date of Patent: Apr. 8, 2014

(54) ION GENERATION APPARATUS

(75) Inventors: Takahiro Hanai, Osaka (JP); Fumimasa Funabiki, Osaka (JP); Tomohisa Ito, Osaka (JP); Yoshihiro Uramoto, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 147 days.

(21) Appl. No.: 13/259,240

(22) PCT Filed: Jan. 29, 2010

(86) PCT No.: PCT/JP2010/051218
§ 371 (c)(1),
(2), (4) Date: Sep. 23, 2011

(87) PCT Pub. No.: WO2010/109944
PCT Pub. Date: Sep. 30, 2010

(65) Prior Publication Data
US 2012/0014840 A1 Jan. 19, 2012

(30) Foreign Application Priority Data
Mar. 26, 2009 (JP) ................................. 2009-076493

(51) Int. Cl.
*A61L 9/00* (2006.01)
(52) U.S. Cl.
USPC .......................................... 422/306; 422/305
(58) Field of Classification Search
USPC ............. 422/22, 24, 123–124, 186.04, 186.3, 422/305, 306
See application file for complete search history.

(56) References Cited

U.S. PATENT DOCUMENTS

| 3,217,470 | A | * | 11/1965 | Omohundro | .................... 96/224 |
|---|---|---|---|---|---|
| 5,893,977 | A | | 4/1999 | Pucci | |
| 7,397,647 | B2 | | 7/2008 | Mizuno et al. | |
| 2004/0218315 | A1 | | 11/2004 | Mizuno et al. | |
| 2005/0163669 | A1 | | 7/2005 | Taylor et al. | |

(Continued)

FOREIGN PATENT DOCUMENTS

| EP | 1671659 A1 | 6/2006 |
|---|---|---|
| JP | 3-266398 A | 11/1991 |

(Continued)

OTHER PUBLICATIONS

International Search Report, dated Apr. 6, 2010, issued in PCT/JP2010/051218.

(Continued)

*Primary Examiner* — Monzer R Chorbaji
(74) *Attorney, Agent, or Firm* — Birch, Stewart, Kolasch & Birch, LLP

(57) ABSTRACT

An ion generation apparatus includes: an air blower including a motor and two impellers attached to the output shafts projecting respectively from both sides of the motor; and two ducts through which air sent through rotation of the two impellers is individually allowed to flow in the same direction, for emitting the air outside. A part of whole of each of the ducts is provided in the laminar flow section where a flow of the air is changed into a laminar flow. Since an ion generating section is provided in each of the laminar flow sections, ions generated by the ion generating section can be efficiently involved in the air, so as to increase a concentration of the ions emitted to inside of a room together with the air.

12 Claims, 9 Drawing Sheets

(56) References Cited

U.S. PATENT DOCUMENTS

| | | |
|---|---|---|
| 2005/0287051 A1 | 12/2005 | Yuen |
| 2006/0024197 A1 | 2/2006 | Park et al. |
| 2006/0279897 A1 | 12/2006 | Mizuno et al. |
| 2007/0274019 A1 | 11/2007 | Nakajima |
| 2008/0138242 A1 | 6/2008 | Park et al. |
| 2008/0252189 A1 | 10/2008 | Regan |
| 2011/0155922 A1 | 6/2011 | Funabiki et al. |

FOREIGN PATENT DOCUMENTS

| | | |
|---|---|---|
| JP | 7-37383 U | 7/1995 |
| JP | 8-62180 A | 3/1996 |
| JP | 3048869 U | 3/1998 |
| JP | 11-304356 A | 11/1999 |
| JP | 2002-78788 A | 3/2002 |
| JP | 2002-352997 A | 12/2002 |
| JP | 2004-3885 A | 1/2004 |
| JP | 2004-87493 A | 3/2004 |
| JP | 2005-61950 A | 3/2005 |
| JP | 2005-76906 A | 3/2005 |
| JP | 2005-100870 A | 4/2005 |
| JP | 2005-116229 A | 4/2005 |
| JP | 2005-214463 A | 8/2005 |
| JP | 2005-147455 A | 9/2005 |
| JP | 2005-328904 A | 12/2005 |
| JP | 2005-339935 A | 12/2005 |
| JP | 2006-35204 A | 2/2006 |
| JP | 3770784 B2 | 4/2006 |
| JP | 2007-114177 A | 5/2007 |
| JP | 2007-242389 A | 9/2007 |
| JP | 2007-294180 A | 11/2007 |
| WO | WO 03/098759 A1 | 11/2003 |
| WO | WO 2006/106594 A1 | 10/2006 |
| WO | WO 2007/131981 A1 | 11/2007 |
| WO | WO 2010/023979 A1 | 3/2010 |

OTHER PUBLICATIONS

Extended European Search Report mailed Nov. 5, 2012, isued in the corresponding European patent application No. 10755745.6.
U.S. Notice of Allowance mailed Jan. 9, 2014 in Copending U.S. Appl. No. 13/061,094.

* cited by examiner

F I G. 6
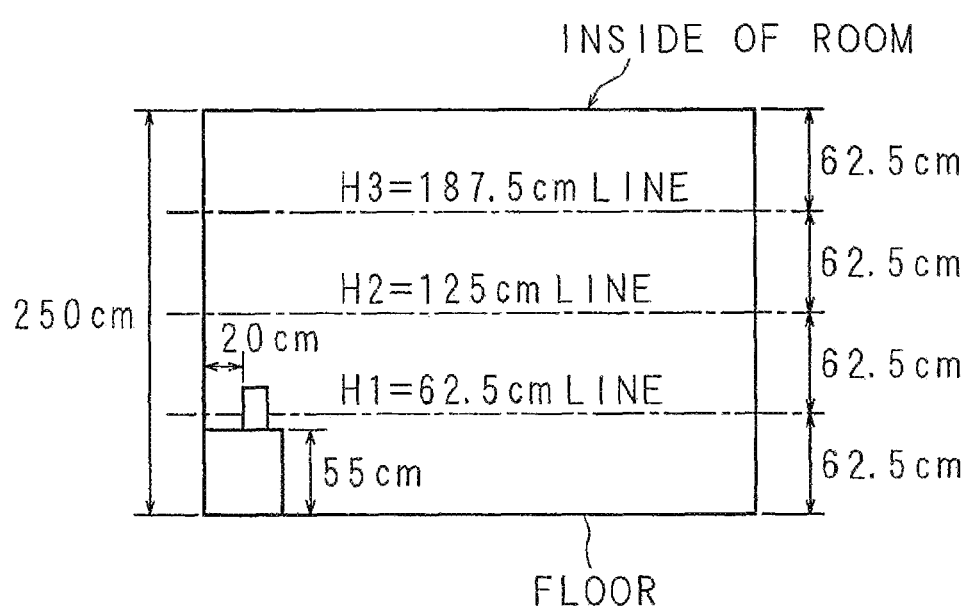

ION GENERATION APPARATUS

This application is the national phase under 35 U.S.C. §371 of PCT International Application No. PCT/JP2010/051218 which has an International filing date of Jan. 29, 2010 and designated the United States of America.

BACKGROUND

1. Technical Field

The present invention relates to an ion generation apparatus that emits ions generated by an ion generating section together with air sent by an air blower to the inside of a room so as to reduce infection with viruses such as influenza virus floating inside the room and to eliminate a smell having been adhered to curtains, clothes and the like.

2. Description of Related Art

Bacteria such as *Serratia marcescens* and bacilli, viruses and the like are floating inside a room. Furthermore, an offensive smell is adhered to curtains, clothes and the like hung inside a room, and therefore, an air cleaner for cleaning the air inside the room is placed in the room. An air cleaner described in Japanese Patent No. 3770784 includes a dielectric for generating positive ions $H^+(H_2O)n$ and negative ions $O_2^-(H_2O)n$, and an air blower for emitting the ions $H^+(H_2O)n$ and $O_2^-(H_2O)n$ generated by the dielectric to the inside of a room.

This air cleaner generates the ions $H^+(H_2O)n$ and $O_2^-(H_2O)n$ simultaneously, so as to generate, through a chemical reaction, hydrogen peroxide $H_2O_2$ or hydroxide radial (.OH) being active species. Since the hydrogen peroxide $H_2O_2$ or hydroxide radical (.OH) exhibits very strong activity, floating bacteria can be eliminated through decomposition by emitting the hydrogen peroxide $H_2O_2$ or hydroxide radical (.OH) to the air of the inside of a room.

SUMMARY

The concentration of the ions emitted to the inside of a room together with air by the air cleaner of Japanese Patent No. 3770784 is 1000 through 2000 ions/cm$^3$, and hence, a disinfecting effect is attained to some extent with respect to the bacteria such as *Serratia marcescens* and bacilli. The number of ions per cm$^3$ is, however, too small for viruses, and an effect to decompose and disinfect viruses is small, and also, an effect to eliminate a smell having been adhered to curtains, clothes and the like is small. Therefore, there has been a demand for an ion generation apparatus capable of increasing the ion concentration inside a room.

In order to increase the ion concentration inside a room, the number of ions generated by an ion generating section provided on a passage of air sent by an air blower may be increased. Even when the number of ion generating sections provided on one passage is increased, however, the number of ions may not be increased by several times. In this case, the number of ions is saturated in the passage, and hence, it is difficult to largely increase the number of ions.

The present invention was devised in consideration of these circumstances. A main object of this invention is to provide an ion generation apparatus that includes: a motor; two impellers attached to the output shafts projecting respectively from both sides of the motor; two passages for individually guiding air flows caused through rotation of the respective impellers along the same direction to emit the air flows outside; and ion generating sections respectively provided on the passages, so as to increase the concentration of ions emitted to the inside of a room together with air, to attain a remarkable disinfecting effect for viruses and to attain a remarkable eliminating effect for a smell having been adhered to curtains, clothes and the like.

The ion generation apparatus of this invention includes an air blower and an ion generating section for generating ions, the ions generated by the ion generating section being emitted outside together with air sent by the air blower. In the ion generation apparatus, the air blower includes: a motor; and two impellers attached to the output shafts projecting respectively from both sides of the motor. The ion generation apparatus further includes two passages through which the air sent through rotation of the two impellers is individually allowed to flow in the same direction, for emitting the air outside. In the ion generation apparatus, the ion generating section is provided in each of the passages.

According to this invention, one motor rotates the two impellers, air flows caused through the rotation of the respective impellers are emitted outside through the two passages, and the ion generating section is provided in each of the passages, and therefore, the concentration of ions emitted to the inside of a room together with the air can be increased. Accordingly, an effect to decompose and disinfect viruses can be increased so as to reduce infection with viruses inside the room. Furthermore, an effect to eliminate a smell having been adhered to curtains, clothes and the like can be increased.

Furthermore, in the ion generation apparatus of this invention, a part or whole of each of the passages preferably includes a laminar flow section where a flow of the air is changed into a laminar flow, and the ion generating section is preferably provided in the laminar flow section.

According to this invention, the ion generating section is provided in each laminar flow section where each of the air flows caused through the rotation of the impellers is changed to a laminar flow. Therefore, the ions generated by the ion generating section can be efficiently involved in the air of the laminar flow passing through each of the passages, so as to increase the concentration of the ions emitted to the inside of the room together with the air. Accordingly, the effect to decompose and disinfect viruses can be increased so as to reduce infection with viruses inside the room. Furthermore, the effect to eliminate a smell having been adhered to curtains, clothes and the like can be increased.

Furthermore, the ion generation apparatus of this invention preferably further includes a rectifier for rectifying the air sent through the rotation of the impellers, and the ion generating section is preferably provided in the rectifier.

According to this invention, since the ions can be efficiently involved in the air of the laminar flow having been rectified by the rectifier, the concentration of ions emitted to the inside of the room together with the air can be increased, so as to increase the disinfecting effect for viruses.

Furthermore, in the ion generation apparatus of this invention, the rectifier is preferably a casing where the impeller is placed.

According to this invention, since the ions can be efficiently involved in the air of the laminar flow passing through a comparatively narrow passage inside the casing, the concentration of ions emitted to the inside of the room together with the air can be further increased.

Furthermore, in the ion generation apparatus of this invention, the casing preferably includes: two arc-shaped guiding walls for guiding the air sent through the rotation of the impellers respectively; and two air outlets respectively opened in a part of the arc-shaped guiding walls toward one direction along a tangential line of the arc-shaped guiding walls, and the ion generating section is preferably provided in each of the arc-shaped guiding walls.

According to this invention, since the ions can be involved in the air of the laminar flow passing through the comparatively narrow passage inside the casing at a high speed, the ions generated by the ion generating section can be more efficiently involved in the air. Also, the concentration of ions emitted to the inside of the room together with the air can be further increased.

Furthermore, in the ion generation apparatus of this invention, each of the passages preferably includes a cylindrical section where an upward flow of the air blown out from each of the air outlets is changed into a laminar flow, and the ion generating section is preferably provided in each cylindrical section.

According to this invention, the laminar flow section is formed in each cylindrical section connected to each air outlet and the ion generating section is provided in each cylindrical section, and hence, the ion generating section can be provided without making a portion around the air blower large, and the ion generation apparatus can be compact.

Furthermore, the ion generation apparatus of this invention preferably further includes two blow-direction changers, each of which is provided at an emitting end of each of the passages, and at least one of the blow-direction changers is preferably removable.

According to this invention, when the directions of the two blow-direction changers are different, a direction for emitting the ions can be changed in accordance with a state of living inside the room, and hence, the ions can be efficiently emitted to the inside of the room.

Furthermore, in the ion generation apparatus of this invention, each of the blow-direction changers preferably includes a blow-direction changing plate for changing a direction of the air emitted outside.

According to this invention, when the directions of the two blow-direction changers are the same, all the ions can be emitted toward the same direction. Alternatively, when the directions of the two blow-direction changers are opposite, a half of the ions can be emitted toward a first direction with the remaining half emitted to a second direction. Therefore, the ions emitted from the two blow-direction changers can be prevented from interfering with each other inside the room.

Furthermore, in the ion generation apparatus of this invention, each of the blow-direction changers preferably includes a rectangular frame section with an inverse trapezoid cross-section, and at least one of the blow-direction changers preferably includes: a first emitting section for emitting the air toward a first direction; and a second emitting section for emitting the air toward a second direction.

According to this invention, the air can be emitted toward the first direction and the second direction. In addition, the quantity of air emitted toward the first direction can be increased or can be set to be the same as the quantity of air emitted toward the second direction. An emitting width toward the first direction or toward both the first direction and the second direction can be increased. Therefore, the ions can be efficiently spread over a wide range in the room in accordance with a state of living inside the room.

Furthermore, in the ion generation apparatus of this invention, at least one of the blow-direction changers preferably includes: a first emitting section for emitting the air toward a first direction; and a second emitting section for emitting the air toward a second direction.

According to this invention, the air can be emitted toward the first direction and the second direction. In addition, the quantity of air emitted toward the first direction can be increased or can be set to be the same as the quantity of air emitted toward the second direction. An emitting width toward the first direction or toward both the first direction and the second direction can be increased. Therefore, the ions can be efficiently spread over a wide range in the room in accordance with a state of living inside the room.

Furthermore, in the ion generation apparatus of this invention, a capacity of one of the first emitting section and the second emitting section is preferably larger than a capacity of the other.

According to this invention, the air can be emitted from at least one of the blow-direction changers toward the first direction and the second direction. In accordance with a state of living inside the room, the quantity of ions emitted toward the first direction can be increased and the emitting width toward the first direction can be increased and the quantity of ions emitted toward the second direction can be reduced and the emitting width toward the second direction can be reduced, so that the ions can be efficiently spread over a wide range in the room. Moreover, the ions can be emitted from each of the two blow-direction changers toward the first direction and the second direction. In this case, in accordance with a state of living inside the room, the quantity of ions emitted toward the first direction can be increased or can be set to be the same as the quantity of ions emitted toward the second direction and an emitting width toward the first direction or toward both the first direction and the second direction can be increased. Therefore, the ions can be efficiently spread over a wide range in the room.

Furthermore, in the ion generation apparatus of this invention, the blow-direction changer preferably includes a frame section, the first emitting section preferably includes a plurality of blow-direction changing plates spaced from each other and opposing each other, and the second emitting section is preferably provided between one of the blow-direction changing plates and an inner face of the frame section.

According to this invention, since the first emitting section for emitting the air toward the first direction and the second emitting section for emitting the air toward the second direction are opened on the passage, dust or the like can be prevented from accumulating in the first and second emitting sections.

Furthermore, in the ion generation apparatus of this invention, the ion generating section is preferably plural in number and provided to be spaced from each other along a direction crossing a flow direction of the air.

According to this invention, the number of portions where the ions generated by the ion generating section are involved in the air of the laminar flow passing through the comparatively narrow passage can be increased, and hence, the ions generated by the ion generating section can be more efficiently involved in the air. Therefore, the concentration of ions emitted from the air outlet together with the air can be further increased.

In the ion generation apparatus of this invention, the ion generating section is preferably plural in number and provided to be spaced from each other along the flow direction.

According to this invention, the number of portions where the ions are involved in the air of the laminar flow passing through the comparatively narrow passage can be increased. Therefore, the ions generated by the ion generating section can be more efficiently involved in the air, and the concentration of ions emitted from the air outlet together with the air can be further increased.

According to this invention, one motor rotates the two impellers, the air flows caused through the rotation of the respective impellers are emitted outside through the two passages, and the ion generating section is provided in each of the passages, and therefore, the concentration of ions emitted to the inside of a room together with the air can be increased.

Accordingly, a disinfecting effect for viruses can be increased so as to reduce infection with viruses inside the room. Furthermore, an effect to eliminate a smell having been adhered to curtains, clothes and the like can be increased.

Furthermore, according to this invention, the ion generating section is provided in each laminar flow section where each of the air flows caused through the rotation of the impellers passes as a laminar flow, and therefore, ions generated by the ion generating section can be efficiently involved in the air passing through each of the passages, so as to increase the concentration of ions emitted to the inside of the room together with the air. Accordingly, the disinfecting effect for viruses can be increased as well as the effect to eliminate a smell having been adhered to curtains, clothes and the like can be increased.

The above and further objects and features will move fully be apparent from the following detailed description with accompanying drawings.

BRIEF DESCRIPTION OF THE SEVERAL VIEWS OF THE DRAWINGS

FIG. 6 is a side sketch illustrating the measurement, performed inside the room, of the air emitted from the blow-direction changers included in the ion generation apparatus installed on the floor of the room.

DETAILED DESCRIPTION

The present invention will now be described with reference to the accompanying drawings illustrating embodiments thereof.

Embodiment 1

Figure 1:
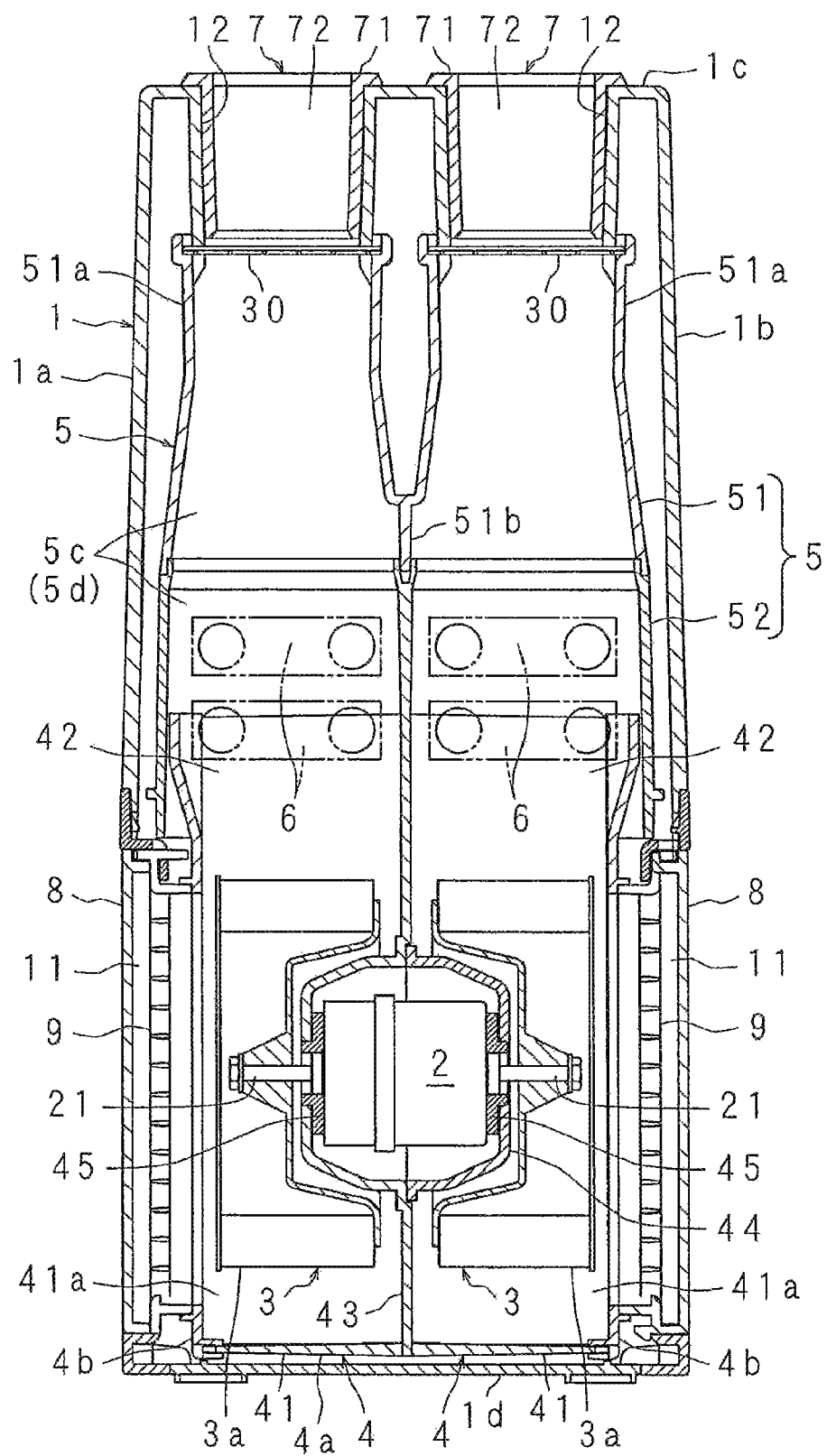
FIG. 1 is a longitudinal cross-sectional front view illustrating a structure of an ion generation apparatus of this invention.
Figure 2:
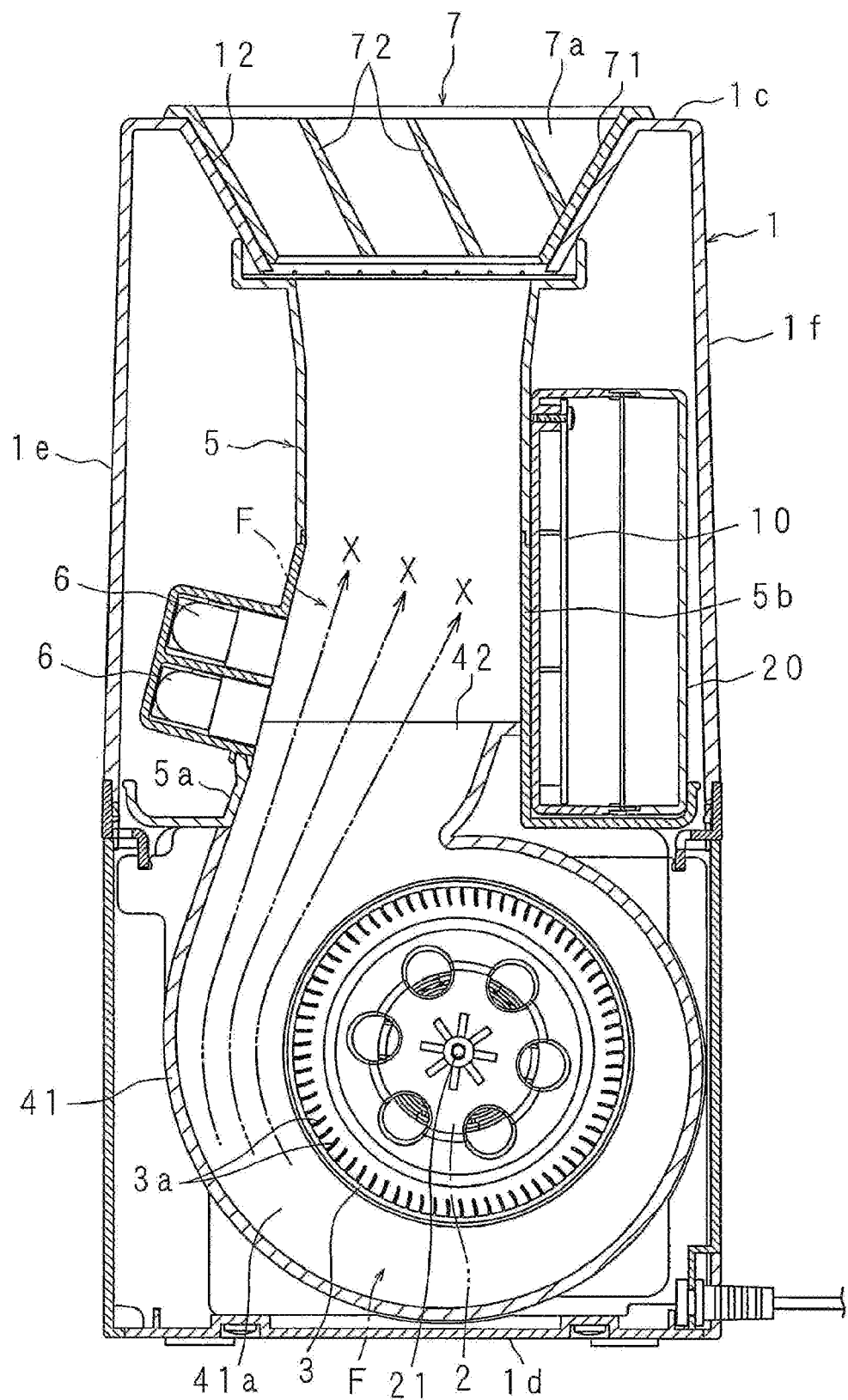
FIG. 2 is a longitudinal cross-sectional side view illustrating the structure of the ion generation apparatus of this invention.
Figure 3:
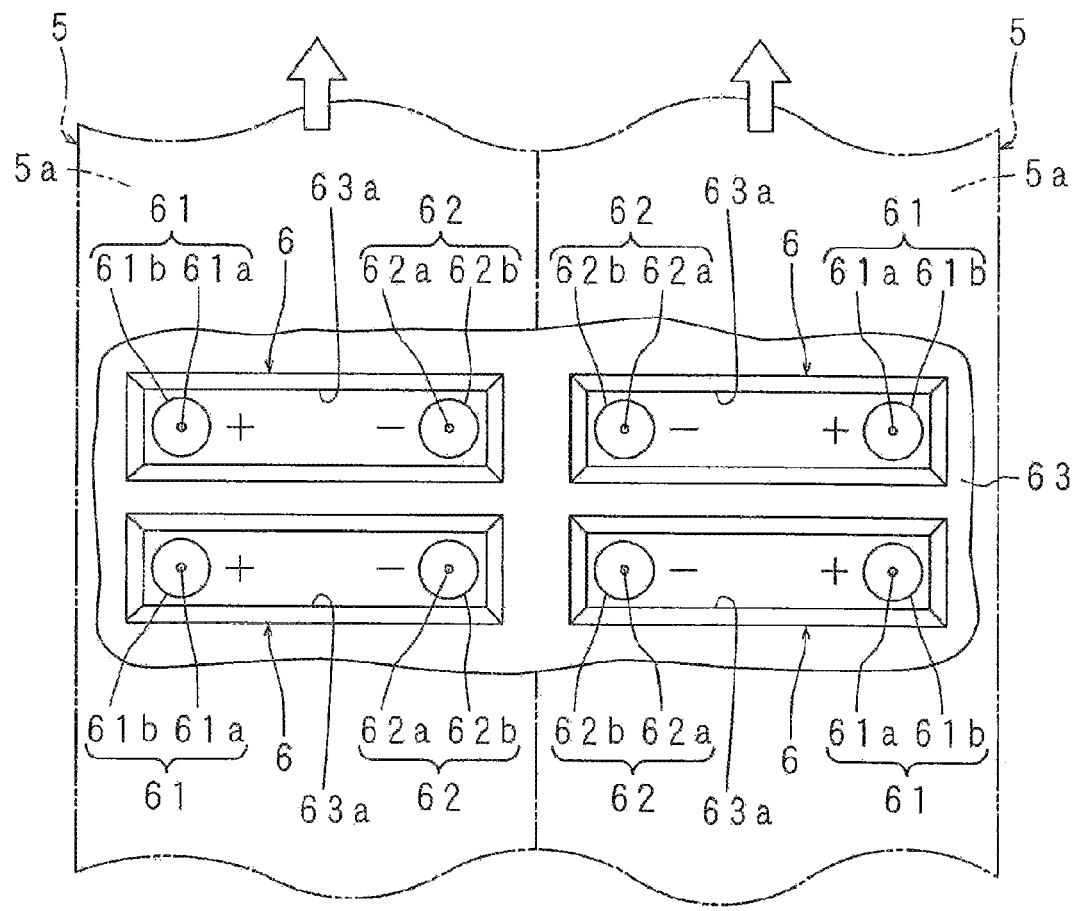
FIG. 3 is a partly omitted front view illustrating the structure of an ion generator included in the ion generation apparatus of this invention.
Figure 4:
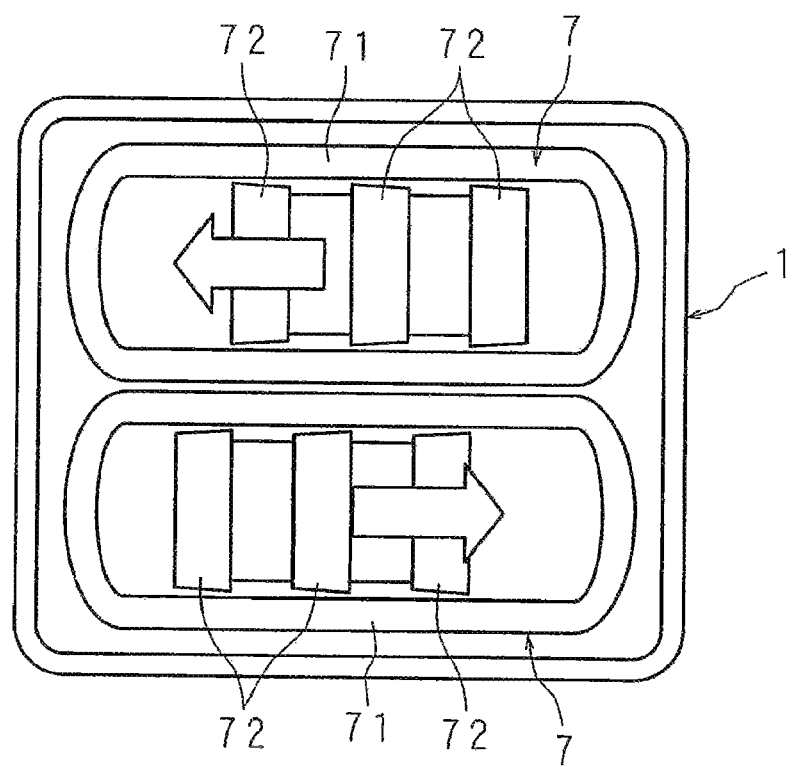
FIG. 4 is a plan view illustrating the structure of the ion generation apparatus of this invention.

FIG. 1 is a longitudinal cross-sectional front view illustrating a structure of an ion generation apparatus of this invention, FIG. 2 is a longitudinal cross-sectional side view illustrating the structure of the ion generation apparatus, FIG. 3 is a partly omitted front view illustrating the structure of an ion generator and FIG. 4 is a plan view illustrating the structure of the ion generation apparatus.

The ion generation apparatus of FIG. 1 includes: a housing 1 having air inlets 11 disposed in lower portions of side walls 1a and 1b spaced from each other and opposing each other and two fit holes 12 disposed in a center portion of a top wall 1c; a motor 2 disposed in a lower portion inside the housing 1; two impellers 3 respectively attached to the output shafts 21 projecting respectively from both sides of the motor 2; two casings 4 rotatably casing the impellers 3; two ducts 5 corresponding to cylindrical sections for individually allowing air flows caused through rotation of the respective impellers 3 to go upward; ion generators 6 each having two ion generating sections 61 and 62 and disposed in the middle of each of the ducts 5; and blow-direction changers 7 removably provided respectively in the fit holes 12. It is noted that the motor 2, the impellers 3 and the casings 4 together form an air blower.

The housing 1 is in a substantially rectangular parallelepiped having: a bottom wall 1d in a rectangular shape in a plan view; a front wall 1e and a rear wall 1f connected to two sides of the bottom wall 1d; the side walls 1a and 1b connected to the other two sides of the bottom wall 1d; and the top wall 1c. The air inlets 11 disposed in the lower portions of the side walls 1a and 1b are provided with filters 8 for allowing air drawn by the impellers 3 through the air inlets 11 to pass therethrough and obtaining clean air by removing extraneous matters from the air. Each of the fit holes 12 disposed on the top wall 1c is in a rectangular shape, a longer direction of which is the forward/backward direction, and has a front inner face inclined forward against the vertical direction and a rear inner face inclined backward against the vertical direction. Furthermore, the housing 1 is separated into an upper section and a lower section in its middle along the upward/downward direction, the casings 4 are provided in the lower section, and the ducts 5 are provided in the upper section.

Each of the impellers 3 is a multiblade impeller having a plurality of blades 3a with rotation center portions thereof against outer edges moving along the rotation direction, namely, is a sirocco impeller in a cylindrical shape. A bearing plate is provided on one end of each of the impellers 3, and each of the output shafts 21 of the motor 2 is attached to a shaft hole formed at the center of the bearing plate, so that air drawn into a center cavity through an opening disposed on the other end may be emitted through a space between the blades 3a disposed on the outer circumference.

Each of the casings 4 includes: an arc-shaped guiding wall 41 for guiding the air flow caused through the rotation of the impeller 3 along the rotation direction of the impeller 3 and increasing the speed of the air flow; and an air outlet 42 opened in a part of the arc-shaped guiding wall 41 upward in one direction along the tangential line of the arc-shaped guiding wall 41. The air outlet 42 is in a rectangular cylindrical shape projecting from a part of the arc-shaped guiding wall 41 toward the one direction along the tangential line of the arc-shaped guiding wall 41 and toward a diagonal direction against the vertical direction. Furthermore, each of the casings 4 includes: a casing main body 4a in a dish shape having an open section for the arc-shaped guiding wall 41 and the air outlet 42; and a cover plate 4b for closing the open side of the casing main body 4a while opening a portion corresponding to the opening of the impeller 3. The casings 4 are integrally connected to each other through opposing portions of the casing main bodies 4a by a connecting wall 43 for partition. Furthermore, each of permeable plates 9 has a plurality of vent holes and is provided between the open portion of the cover plate 4b and the filter 8. It is noted that air passages 41a, each of which is disposed between the circumferential face of each of the impellers 3 and the corresponding arc-shaped guiding wall 41 and the front wall 5a, work respectively as a laminar flow section F.

In a portion of the connecting wall 43 corresponding to the motor 2, a recess depressed toward one casing main body 4a is provided, so that a supporting plate 44 in a dish shape may be attached to the edge of the recess. The motor 2 is held between center portions of the recess and the supporting plate 44 with rubber plates 45 sandwiched therebetween, output shafts 21 are inserted through shaft holes formed respectively in the center portions of the recess and the supporting plate 44, and the impellers 3 are respectively attached to the output shafts 21. Furthermore, the upper end of the connecting wall 43 extends beyond the casings 4.

Each of the ducts 5 is a rectangular cylindrical section having a lower end connected to the air outlet 42, an upper end connected to the fit hole 12 and a narrowed portion in the middle along the upward/downward direction. Furthermore, each of the ducts 5 includes: a front wall 5a extending from the air outlet 42 in one direction along the tangential line of the arc-shaped guiding wall 41; a rear wall 5b extending from the air outlet 42 in substantially a vertical direction; and two side walls 5c and 5d respectively connected to the front wall 5a and the rear wall 5b and extending substantially a vertical direction. Each of the ducts 5 has the laminar flow section F on the side of the front wall 5a facing the impeller 3, so that air blown through the air outlet 42 may be changed into a laminar flow along the front wall 5a and the side walls 5c and 5d so as to make it flow along the vertical direction.

Each of the front walls 5a is provided with a through hole correspondingly to the ion generating sections 61 and 62, and the ion generators 6 are attached to be fit in the through hole. Each of the rear walls 5b is provided with: a circuit board 10 connected to the motor 2, the ion generator 6 and an electric line; and a cover 20 covering the circuit board 10. Also, the ducts 5 are separated, in the middle portion thereof along the upward/downward direction, into a duct upper section 51 and a duct lower section 52. The duct lower section 52 is in a rectangular cylindrical shape partitioned by the connecting wall 43 in the center portion thereof along the lateral direction. The duct upper section 51 includes rectangular cylindrical portions 51a arranged adjacently to be spaced from each other in the lateral direction with lower ends thereof integrally connected to each other by a connecting section 51b and partitioned by the connecting section 51b and the connecting wall 43. Furthermore, protective nets 30 for preventing external insertion of extraneous matters such as a finger are provided in upper end portions of the duct upper section 51.

Each of the ion generators 6 includes: two ion generating sections 61 and 62 spaced from each other along a direction crossing the flow direction of the air flow caused through the rotation of the impeller 3; a power supply section for supplying a voltage to the ion generating sections 61 and 62; and a holding body 63 for holding the ion generating sections 61 and 62 and the power supply section. In each of the ion generators 6, the power supply section supplies a voltage to the ion generating sections 61 and 62, so as to cause corona discharge in the ion generating sections 61 and 62 and to generate ions.

The ion generating sections 61 and 62 include discharge electrode projections 61a and 62a in an acute shape, and induction electrode rings 61b and 62b respectively surrounding the discharge electrode projections 61a and 62a, so that the discharge electrode projections 61a and 62a may be disposed at the centers of the induction electrode rings 61b and 62b, respectively. In each of the ion generators 6, one ion generating section 61 generates positive ions and the other ion generating section 62 generates negative ions.

The two ion generators 6 are held by one holding body 63. The two ion generators 6 are attached to the front wall 5a of each of the ducts 5 to be arranged adjacently and spaced from each other in the flow direction. Furthermore, the ion generating sections 61 and 62 of the two ion generators 6 are arranged adjacently along a direction crossing the flow direction to have the same polarity on the adjacent sides, and the ion generating sections 61 and 62 of each of the ion generators 6 face one of the ducts 5 through the through hole. Moreover, the holding body 63 has, on a side attached to each of the ducts 5, four openings 63a correspondingly to the ion generating sections 61 and 62, and the ion generating sections 61 and 62 are respectively provided in the openings 63a.

Each of the blow-direction changers 7 includes a rectangular frame section 71 having a cross-section in the forward/backward direction of an inverse trapezoid and a plurality of blow-direction changing plates 72 arranged adjacently within the rectangular frame section 71 to be spaced from one another in the forward/backward direction and inclined against the vertical direction in one direction along the forward/backward direction. The blow-direction changers 7 are in the same shape. Front and rear walls of each of rectangular frame sections 71 are inclined against the vertical direction along the forward and backward directions, respectively.

The ion generation apparatus having the aforementioned structure is installed in a room. The impellers 3 are rotated by driving the motor 2 of the air blower, the air inside the room is drawn through the air inlets 11 disposed respectively on the both sides into the two casings 4, and extraneous matters such as dust are removed from the drawn air by the filters 8. At this point, the air drawn into the casings 4 is rectified by the arc-shaped guiding walls 41 while forming air flows flowing along the arc-shaped guiding walls 41 disposed outside the impellers 3. The rectified air is changed into laminar flows at the laminar flow sections F of each of the air passages 41a. The air of the laminar flows flow along the arc-shaped guiding walls 41 to the air outlets 42 as illustrated with alternate dot and two short dashes arrows X in FIG. 2 and is blown into the ducts 5 through the air outlets 42.

Each of the laminar flow sections F is present in the air passage 41a on a side, in a side view, where the front wall 5a of the duct 5 and the arc-shaped guiding wall 41 face the impeller 3. The laminar flow of the air, as illustrated with the arrows X of FIG. 2, passes through the laminar flow sections F, each of which is surrounded by the front wall 5a and the side walls 5c and 5d. The ion generators 6 are provided in the front walls 5a where the air passes as such a laminar flow. As described above, the positive and negative ions generated by the ion generating sections 61 and 62 of the ion generators 6 can be efficiently involved in the air passing as the laminar flow through comparatively narrow paths along the front walls 5a. Furthermore, since the middle portion along the upward/downward direction of each of the ducts 5 is narrowed so as to make the air flow at a high speed, the positive ions and the negative ions can be efficiently involved in the air. Moreover, since a plurality of ion generators 6 are spaced from each other along the air flow direction and the number of portions where the ions are involved in the air is large, the ions can be efficiently involved in the air. Incidentally, although the ion generators 6 face each of the air outlets 42 and are provided on each of the front walls 5a corresponding respectively to the ends of the arc-shaped guiding walls 41 in this embodiment, this invention is not limited to this structure. The ion generators 6 may be provided in other positions as far as they face the laminar flow sections F where the laminar flows of the air pass within the ducts 5 as illustrated with the arrows X. For example, the ion generators 6 may be provided, in a side view, in arc portions where a constant curvature of a circular portion of the arc-shaped guiding walls 41 is gradually reduced upward or in straight portions where the curvature is infinite.

Incidentally, in employing the structure where the two ion generators 6 are provided on each of the front walls 5a of the ducts 5 to be spaced from each other in the flow direction, when an ion concentration per $cm^3$ in air emitted to the inside of a room was measured, an ion concentration of approximately 7000 ions/$cm^3$ could be attained. Accordingly, the disinfecting effect for viruses inside the room and the eliminating effect for a smell having been adhered to curtains, clothes and the like can be improved.

It has conventionally known to send positive ions $H^+(H_2O)m$ (wherein m is an arbitrary integer) and negative ions $O_2^-(H_2O)n$ (wherein n is an arbitrary integer) into the air for disinfecting floating bacteria through a reaction of the ions. Since the ions are recombined with each other to disappear, however, even if a high concentration can be attained in the vicinity of poles of an ion generating device, the concentration is abruptly reduced as a sending distance is increased. Accordingly, even if an ion concentration of tens of thousands of ions/$cm^3$ can be attained in a space with a small capacity like an experimental device, a concentration attained in a large space such as an actual room or an operation space is limited to 2,000 through 3,000 ions/$cm^3$ at the most.

Figure 5:
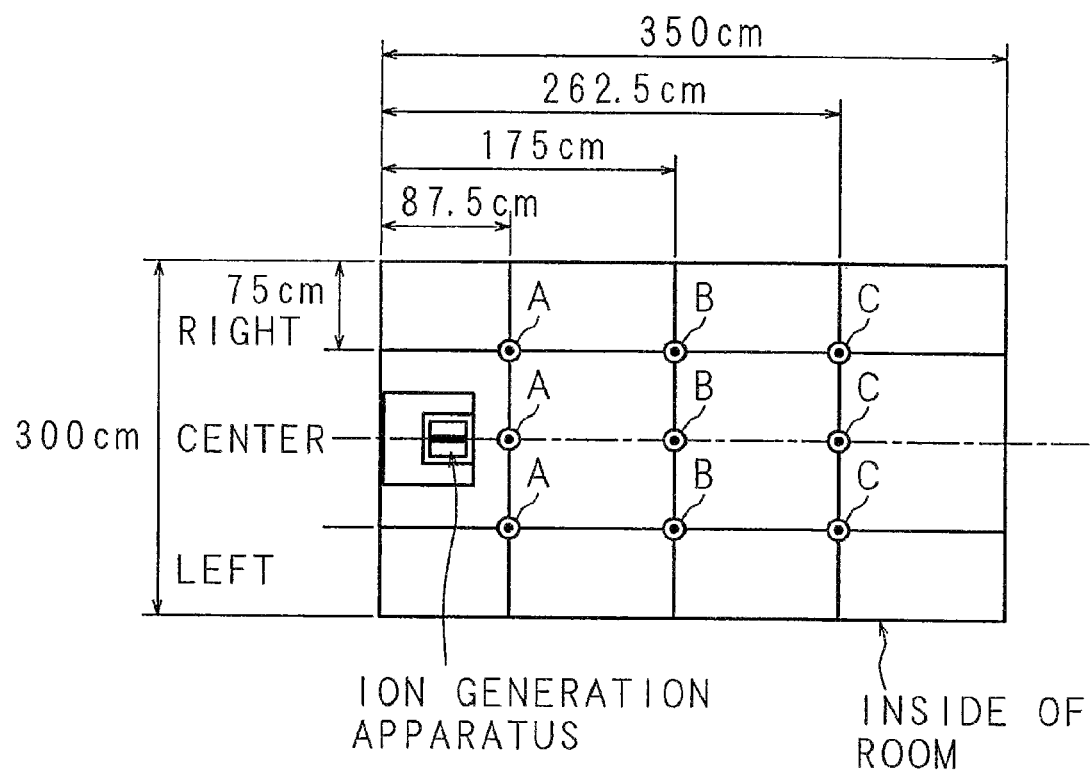
FIG. 5 is a plan sketch illustrating measurement, performed inside a room, of air emitted from blow-direction changers included in the ion generation apparatus installed on the floor of the room.

On the other hand, the present inventors have found that avian influenza viruses can be removed by 99% in 10 minutes at a laboratory level when the ion concentration is 7,000 ions/$cm^3$ and by 99.9% when the concentration is 50,000 ions/$cm^3$. Assuming that the viruses are present in the air in a rate of 1,000 viruses/$cm^3$, these removal rates mean that merely 10 viruses/$cm^3$ and 1 virus/$cm^3$ remain respectively. In other words, when the ion concentration is increased from 7,000 ions/$cm^3$ to 50,000 ions/$cm^3$, the number of remaining viruses can be reduced by 1/10.

Therefore, it is understood that it is very significant for infection prevention and environment clarification not only to send ions at a high concentration to a living space or an operation space where people live but also to attain a high ion concentration over the whole space.

FIG. 5 is a plan sketch illustrating measurement, performed inside a room, of air emitted from the blow-direction changers included in the ion generation apparatus of this invention installed on the floor of the room, and FIG. 6 is a side sketch illustrating the measurement, performed inside the room, of the air emitted from the blow-direction changers included in the ion generation apparatus of this invention installed on the floor of the room. Table 1 shows data obtained as a result of the measurement of ion concentrations inside the room where the ion generation apparatus of Embodiment 1 is installed.

TABLE 1

TABLE 1

| | | DISTANCE FROM WALL (DISTANCE FROM REAR FACE OF ION GENERATION APPARATUS TO WALL: 20 cm) | | | | | | AVERAGE VALUE | |
|---|---|---|---|---|---|---|---|---|---|
| | | 87.5 cm | | 175 cm | | 262.5 cm | | PER HEIGHT | |
| HEIGHT ABOVE FLOOR | PLAN POINT | POSITIVE ION [ions/cm³] | NEGATIVE ION [ions/cm³] | POSITIVE ION [ions/cm³] | NEGATIVE ION [ions/cm³] | POSITIVE ION [ions/cm³] | NEGATIVE ION [ions/cm³] | POSITIVE ION [ions/cm³] | NEGATIVE ION [ions/cm³] |
| 187.5 cm | RIGHT (75 cm FROM WALL) | 51,200 | 67,500 | 27,200 | 29,000 | 8,000 | 9,000 | 24,022 | 26,544 |
| | CENTER | 29,100 | 35,300 | 22,300 | 21,400 | 9,900 | 9,400 | | |
| | LEFT (75 cm FROM WALL) | 28,000 | 29,700 | 31,600 | 29,600 | 8,900 | 8,000 | | |
| 125 cm | RIGHT (75 cm FROM WALL) | 16,100 | 15,800 | 18,100 | 18,900 | 9,000 | 9,000 | 12,156 | 13,111 |
| | CENTER | 9,700 | 12,700 | 10,900 | 10,500 | 10,400 | 11,100 | | |
| | LEFT (75 cm FROM WALL) | 12,300 | 15,100 | 13,300 | 14,400 | 9,600 | 10,500 | | |
| 62.5 cm | RIGHT (75 cm FROM WALL) | 13,000 | 14,400 | 13,000 | 15,200 | 11,400 | 11,500 | 11,333 | 12,067 |
| | CENTER | 8,900 | 9,000 | 10,000 | 10,700 | 11,600 | 13,100 | | |
| | LEFT (75 cm FROM WALL) | 10,500 | 11,900 | 11,600 | 10,900 | 12,000 | 11,900 | | |
| AVERAGE VALUE PER POINT | RIGHT (75 cm FROM WALL) | 26,767 | 32,567 | 19,433 | 21,033 | 9,467 | 9,833 | 15,837 | 17,241 |
| | CENTER | 15,900 | 19,000 | 14,400 | 14,200 | 10,633 | 11,200 | | |
| | LEFT (75 cm FROM WALL) | 16,933 | 18,900 | 18,833 | 18,300 | 10,167 | 10,133 | | |

The ion concentrations attained by the ion generation apparatus of Embodiment 1 were measured in points A through C in the room at heights H1 through H3 above the floor of the room, and the results listed in Table 1 were obtained. In FIGS. 5 and 6, the room has a floor area of 300 cm×350 cm and a height of 250 cm, and the ion generation apparatus is installed on a table disposed to be away by 20 cm from one of walls with a length of 300 cm and by 55 cm above the floor.

The measurement points A are points that are away by 87.5 cm from one of the walls with the length of 300 cm and are away by 75 cm respectively from the walls with the length of 350 cm and at a center of these walls. The measurement points B are points that are away by 175 cm from one of the walls with the length of 300 cm and are away by 75 cm respectively from the walls with the length of 350 cm and at a center of these walls. The measurement points C are points that are away by 262.5 cm from one of the walls with the length of 300 cm and are away by 75 cm respectively from the walls with the length of 350 cm and at a center of these walls. Furthermore, in each of the measurement points A through C, the height H1 is 62.5 cm, the height H2 is 125 cm and the height H3 is 187.5 cm. Also, the generation capacity of the ion generation apparatus is 1.2 $m^3$/min.

It is understood from the measurement results listed in Table 1 that the ion concentrations can be increased up to 21,400 ions/$cm^3$ through 67,500 ions/$cm^3$ in the measurement points A and B at the height H3 and that the lowest ion concentration obtained in the measurement points C at the height H3 can be increased up to 8,000 ions/$cm^3$. Furthermore, average values of the ion concentrations at the height H3 in the measurement points A through C are increased up to 24,022 ions/$cm^3$ and 26,544 ions/$cm^3$, average values of the ion concentrations at the height H2 are increased up to 12,156 ions/$cm^3$ and 13,111 ions/$cm^3$, and average values of the ion concentrations at the height H1 are increased up to 11,333 ions/$cm^3$ and 12,067 ions/$cm^3$. Moreover, average values of the ion concentrations obtained in the respective measurement points A variously away from the wall in the lateral direction are increased up to 15,900 ions/$cm^3$ through 32,567 ions/$cm^3$, average values of the ion concentrations obtained in the respective measurement points B variously away from the wall in the lateral direction are increased up to 14,200 ions/$cm^3$ through 21,033 ions/$cm^3$, and average values of the ion concentrations obtained in the respective measurement points C variously away from the wall in the lateral direction are increased up to 9,833 ions/$cm^3$ through 11,200 ions/$cm^3$. As is obvious from the measurement results listed in Table 1, it is proved that the concentration of ions emitted to the inside of the room can be increased.

Embodiment 2

Figure 7:
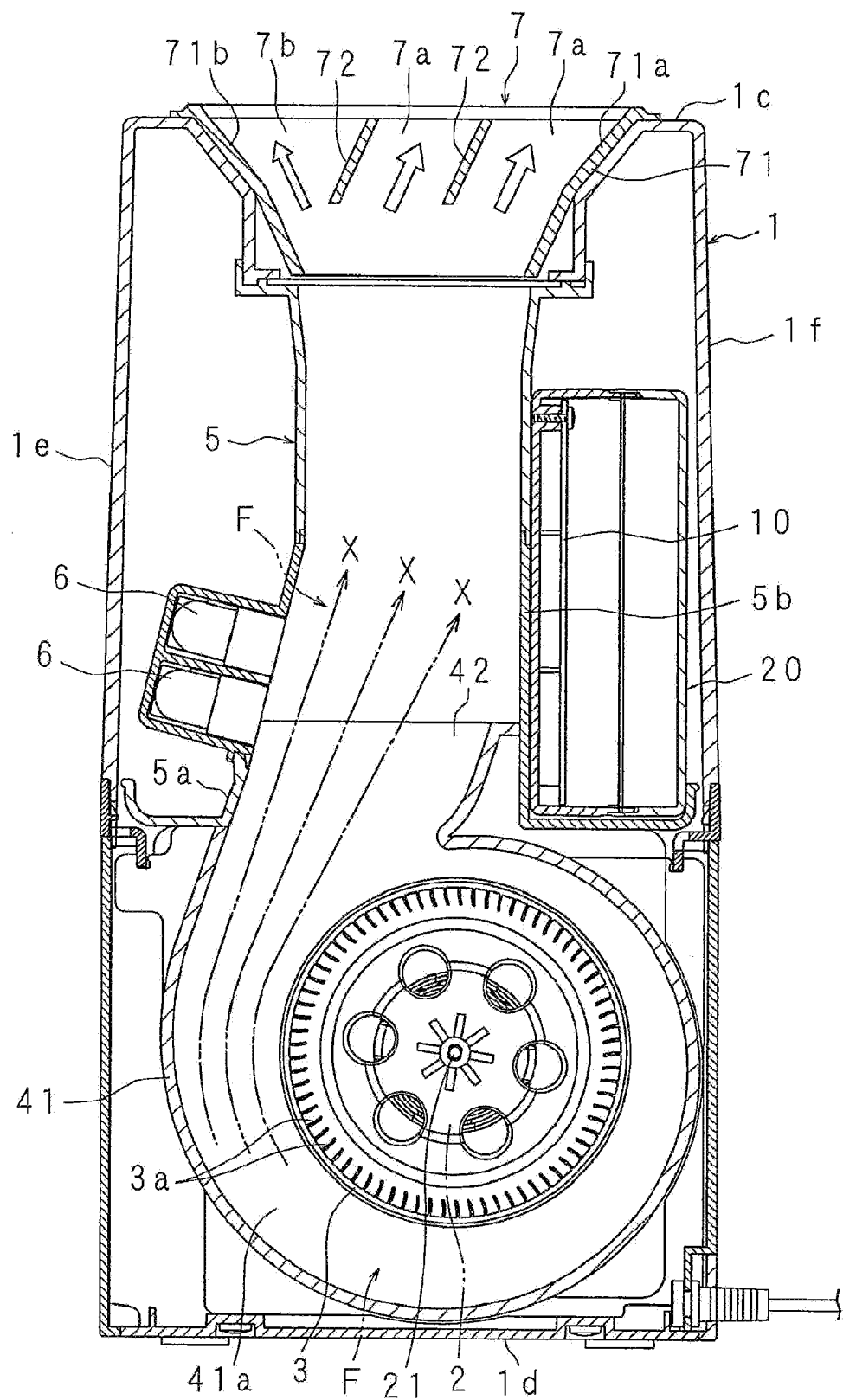
FIG. 7 is a longitudinal cross-sectional side view illustrating another structure of the ion generation apparatus of this invention.
Figure 8:
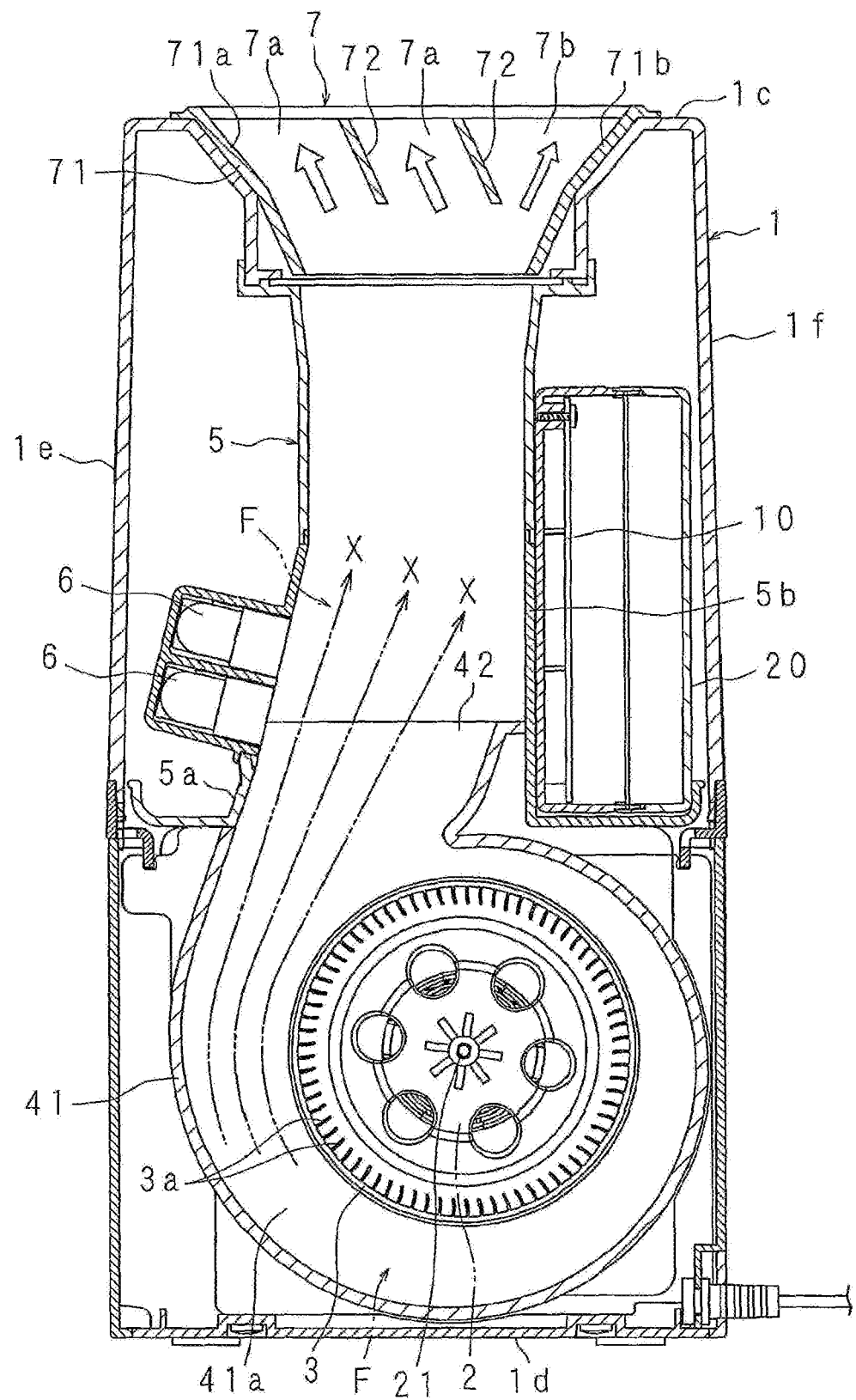
FIG. 8 is a longitudinal cross-sectional side view illustrating another structure of the ion generation apparatus of this invention.
Figure 9:
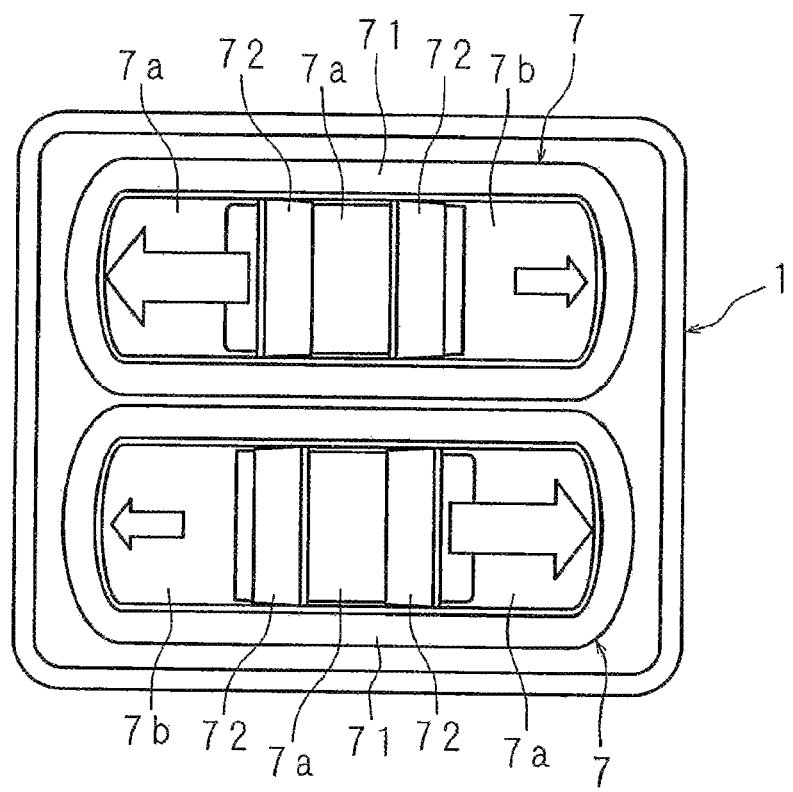
FIG. 9 is a plan view illustrating another structure of the ion generation apparatus of this invention.

FIGS. 7 and 8 are longitudinal cross-sectional side views illustrating another structure of the ion generation apparatus of this invention, and FIG. 9 is a plan view illustrating another structure of the ion generation apparatus.

In the ion generation apparatus of FIGS. 7 through 9, each of blow-direction changers 7 including a rectangular frame section 71 having a cross-section in the forward/backward direction of an inverse trapezoid is provided with first emitting sections 7a for allowing air to blow toward a first direction and a second emitting section 7b for allowing the air to blow toward a second direction.

Each of the rectangular frame sections 71 is in a substantially elliptical cylindrical shape having: a front wall 71a and a rear wall 71b inclined against the vertical direction in forward and backward directions; and side walls connected to the front wall 71a and the rear wall 71b and extending in the vertical direction. Each of the rectangular frame sections 71 is fit removably upward in each of the fit holes 12 of a housing 1.

The first emitting sections 7a are arranged adjacently within each of the rectangular frame sections 71 to be spaced from each other in the forward/backward direction, and are formed between two blow-direction changing plates 72 inclined against the vertical direction in one direction along the forward/backward direction and between one of the blow-direction changing plates 72 and the front wall 71a.

The second emitting section 7b is formed between the inclined rear wall 71a of the rectangular frame section 71 and one of the blow-direction changing plates 72. The rectangular frame section 71 and the blow-direction changing plates 72 are integrally formed from a synthetic resin material.

The capacities attained by the first and second emitting sections 7a and 7b are set so that the capacity attained by the first emitting sections 7a may be larger than that attained by the second emitting section 7b in a ratio of approximately 3:1.

In the ion generation apparatus having the aforementioned structure, the air emitted upward from ducts 5 is emitted toward the first direction by the first emitting sections 7a as well as toward the second direction by the second emitting sections 7b, and thus is emitted through the first and second emitting sections 7a and 7b to the inside of a room. Therefore, emitting widths (along the lateral direction) toward the first direction and the second direction can be increased, and ions can be emitted over a wide range of the space.

Since the capacity of the first emitting sections 7a is larger than the capacity of the second emitting sections 7b in the blow-direction changers 7, when the directions of the first emitting sections 7a and the directions of the second emitting sections 7b are respectively set to be the same between the blow-direction changers 7, the capacity toward the first direction can be increased, for example, at a ratio of 3:1 with the capacity toward the second direction reduced, and the air can be emitted over a wide range by thus increasing the emitting widths toward the first direction and the second direction. Furthermore, when the directions of the first emitting sections 7a are set to be opposite in the blow-direction changers 7 as illustrated in FIG. 9, the capacity toward the first direction and the capacity toward the second direction can be made equal, and the air can be emitted over a wide range by increasing the emitting widths toward the first direction and the second direction.

Moreover, since the first and second emitting sections 7a and 7b of the blow-direction changers 7 are opened on the ducts 5, it is possible to prevent dust or the like from accumulating in the first and second emitting sections 7a and 7b.

Table 2 shows data obtained as a result of measurement of ion concentrations attained in a room by the ion generation apparatus of Embodiment 2. The measurement conditions and the measurement points are the same as those of Embodiment 1 illustrated in FIGS. 5 and 6.

When the ion concentrations attained by the ion generation apparatus of Embodiment 2 were measured in the points A through C at the heights H1 through H3 in the room, the results listed in Table 2 were obtained.

TABLE 2

| HEIGHT ABOVE FLOOR | PLAN POINT | DISTANCE FROM WALL (DISTANCE FROM REAR FACE OF ION GENERATION APPARATUS TO WALL: 20 cm) | | | | | | AVERAGE VALUE PER HEIGHT | |
| --- | --- | --- | --- | --- | --- | --- | --- | --- | --- |
| | | 87.5 cm | | 175 cm | | 262.5 cm | | | |
| | | POSITIVE ION [ions/cm$^3$] | NEGATIVE ION [ions/cm$^3$] | POSITIVE ION [ions/cm$^3$] | NEGATIVE ION [ions/cm$^3$] | POSITIVE ION [ions/cm$^3$] | NEGATIVE ION [ions/cm$^3$] | POSITIVE ION [ions/cm$^3$] | NEGATIVE ION [ions/cm$^3$] |
| 187.5 cm | RIGHT (75 cm FROM WALL) | 30,100 | 23,300 | 28,900 | 32,900 | 14,400 | 13,700 | 30,411 | 34,333 |
| | CENTER | 91,900 | 123,200 | 18,200 | 21,800 | 11,300 | 12,500 | | |
| | LEFT (75cm FROM WALL) | 38,700 | 38,000 | 27,600 | 30,400 | 12,600 | 13,200 | | |
| 125 cm | RIGHT (75 cm FROM WALL) | 13,200 | 15,300 | 18,900 | 26,000 | 10,900 | 12,800 | 14,167 | 16,056 |
| | CENTER | 10,700 | 14,000 | 14,100 | 15,400 | 11,500 | 11,400 | | |
| | LEFT (75 cm FROM WALL) | 14,900 | 15,500 | 21,000 | 20,800 | 12,300 | 13,300 | | |
| 62.5 cm | RIGHT (75 cm FROM WALL) | 15,000 | 17,400 | 15,700 | 14,400 | 12,300 | 13,900 | 12,233 | 13,611 |
| | CENTER | 9,500 | 10,900 | 11,000 | 11,300 | 11,700 | 13,300 | | |
| | LEFT (75 cm FROM WALL) | 11,800 | 15,000 | 10,300 | 13,600 | 12,800 | 12,700 | | |
| AVERAGE VALUE PER POINT | RIGHT (75 cm FROM WALL) | 19,433 | 18,667 | 21,167 | 24,433 | 12,533 | 13,467 | 18,937 | 21,333 |
| | CENTER | 37,367 | 49,367 | 14,433 | 16,167 | 11,500 | 12,400 | | |
| | LEFT (75 cm FROM WALL) | 21,800 | 22,833 | 19,633 | 21,600 | 12,567 | 13,067 | | |

It is understood from the measurement results listed in Table 2 that the ion concentrations can be increased up to 18,200 ions/cm$^3$ through 123,200 ions/cm$^3$ in the measurement points A and B at the height H3 and that the lowest ion concentration obtained in the measurement point A at the height H1 can be increased up to 9,500 ions/cm$^3$. Furthermore, average values of the ion concentrations at the height H3 in the measurement points A through C are increased up to 30,411 ions/cm$^3$ and 34,333 ions/cm$^3$, average values of the ion concentrations at the height H2 are increased up to 14,167 ions/cm$^3$ and 16,056 ions/cm$^3$, and average values of the ion concentrations at the height H1 are increased up to 12,233 ions/cm$^3$ and 13,611 ions/cm$^3$. Moreover, average values of the ion concentrations obtained in the respective measurement points A variously away from the wall in the lateral direction are increased up to 18,667 ions/cm$^3$ through 49,367 ions/cm$^3$, average values of the ion concentrations obtained in the respective measurement points B variously away from the wall in the lateral direction are increased up to 14,433 ions/cm$^3$ through 24,433 ions/cm$^3$, and average values of the ion concentrations obtained in the respective measurement points C variously away from the wall in the lateral direction are increased up to 11,500 ions/cm$^3$ through 13,467 ions/cm$^3$. As is obvious from the measurement results listed in Table 2, it is proved that the concentration of ions emitted to the inside of the room can be increased.

Furthermore, in the ion generation apparatus of Embodiment 2, the concentrations of ions emitted to the inside of the room can be more improved than in the ion generation apparatus of Embodiment 1 as is apparent from Tables 1 and 2, and the ions can be efficiently spread over a wide range in the room.

Since the remaining structure and function are the same as those described in Embodiment 1, like reference numerals are used to refer to like elements so as to omit the detailed description of the elements and description of their functions and effects.

Incidentally, the laminar flow sections F where the flows of the air sent through the rotation of the impellers 3 are changed into laminar flow are included in the ducts 5 and the ion generating sections 61 and 62 are provided in the laminar flow sections F of the ducts 5 in the aforementioned embodiments. Instead, the ion generating sections 61 and 62 may be provided in the arc-shaped guiding walls including the laminar flow sections F where the flows of the air sent through the rotation of the impellers 3 are changed into laminar flow, and thus, the positions of the ion generating sections are not particularly specified.

Moreover, although the two ion generators 6 spaced from each other along the flow direction are arranged adjacently in the positions inside the two ducts 5 crossing the flow direction in the aforementioned embodiments, the ion generators 6 of the two passages may be spaced from each other along the flow direction.

Furthermore, although the two blow-direction changers 7 are removable in the aforementioned embodiments, one of the blow-direction changers 7 may be fixed on or integrated with the housing 1 with the other blow-direction changer 7 removable.

Also, although each of the blow-direction changers 7 includes the rectangular frame section 71 in the aforementioned embodiments, each of the blow-direction changers 7 may include one blow-direction changing plate 72 for changing the direction for emitting the air or a plurality of blow-direction changing plates 72 connected to one another to be spaced from one another.

The invention claimed is:

1. An ion generation apparatus, comprising:
   an air blower including a motor and two impellers;
   two passages through which air sent through rotation of the two impellers is individually allowed to flow in the same direction, for emitting the air outside;
   two blow-direction changers, each of which is provided at an emitting end of each of the passages; and
   an ion generating section provided in each of the passages for generating ions emitted outside together with the air sent by the air blower,
   wherein at least one of the blow-direction changers includes:
   a first emitting section for emitting the air toward a first direction; and
   a second emitting section for emitting the air toward a second direction.

2. The ion generation apparatus according to claim 1,
   wherein a part or whole of each of the passages includes a laminar flow section where a flow of the air is changed into a laminar flow,
   wherein the ion generating section is provided in the laminar flow section.

3. The ion generation apparatus according to claim 1,
   further comprising a rectifier for rectifying the air sent through the rotation of the impeller,
   wherein the ion generating section is provided in the rectifier.

4. The ion generation apparatus according to claim 3, wherein the rectifier includes:
   two arc-shaped guiding walls for guiding the air sent through the rotation of the impellers respectively; and
   two air outlets respectively opened in a part of the arc-shaped guiding walls toward one direction along a tangential line of the arc-shaped guiding walls,
   wherein the ion generating section is provided in each of the arc-shaped guiding walls.

5. The ion generation apparatus according to claim 4,
   wherein each of the passages includes a cylindrical section where upward flow of the air blown out from each of the air outlets is changed into a laminar flow,
   wherein the ion generating section is provided in the cylindrical section.

6. The ion generation apparatus according to claim 1,
   wherein at least one of the blow-direction changers is removable.

7. The ion generation apparatus according to claim 1,
   wherein each of the blow-direction changers includes a blow-direction changing plate for changing a direction of the air emitted outside.

8. The ion generation apparatus according to claim 7,
   wherein each of the blow-direction changers includes a rectangular frame section with an inverse trapezoid cross-section.

9. The ion generation apparatus according to claim 1,
   wherein a capacity of one of the first emitting section and the second emitting section is larger than a capacity of the other.

10. The ion generation apparatus according to claim 1,
    wherein the blow-direction changer includes a frame section,
    wherein the first emitting section includes a plurality of blow-direction changing plates spaced from each other and opposing each other,
    wherein the second emitting section is provided between one of the blow-direction changing plates and an inner face of the frame section.

11. The ion generation apparatus according to claim 1,
    wherein the ion generating section is plural in number and provided to be spaced from each other along a direction crossing a flow direction of the air.

12. The ion generation apparatus according to claim 11,
    wherein the ion generating section is plural in number and provided to be spaced from each other along the flow direction.

* * * * *